(12) United States Patent
Cho et al.

(10) Patent No.: US 10,399,928 B2
(45) Date of Patent: Sep. 3, 2019

(54) METHOD OF CONVERTING A NITRILE FUNCTIONAL GROUP INTO A HYDROXAMIC FUNCTIONAL GROUP BY USING A PEROXOCOBALT COMPLEX AT ROOM TEMPERATURE AND NORMAL PRESSURE

(71) Applicant: DAEGU GYEONGBUK INSTITUTE OF SCIENCE AND TECHNOLOGY, Daegu (KR)

(72) Inventors: Jaeheung Cho, Daegu (KR); Hyeon Ju Noh, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 16/156,967

(22) Filed: Oct. 10, 2018

(65) Prior Publication Data

US 2019/0106382 A1 Apr. 11, 2019

(30) Foreign Application Priority Data

Oct. 11, 2017 (KR) .................. 10-2017-0130178

(51) Int. Cl.
| | |
|---|---|
| *C07C 259/06* | (2006.01) |
| *C07C 259/08* | (2006.01) |
| *B01J 31/22* | (2006.01) |
| *B01J 31/18* | (2006.01) |
| *C07C 259/10* | (2006.01) |

(52) U.S. Cl.
CPC ......... *C07C 259/06* (2013.01); *B01J 31/1815* (2013.01); *B01J 31/2208* (2013.01); *C07C 259/08* (2013.01); *C07C 259/10* (2013.01); *B01J 2531/845* (2013.01)

(58) Field of Classification Search
None
See application file for complete search history.

(56) References Cited

U.S. PATENT DOCUMENTS

2018/0282333 A1* 10/2018 Bot R .................. C07D 471/18

FOREIGN PATENT DOCUMENTS

KR 20170083680 * 7/2017

OTHER PUBLICATIONS

Shin ("Reactivity of a Cobalt(III)-Hydroperoxo Complex in Electrophilic Reactions" Inorganic Chemsitry, 2016, 55, p. 12391-12399) (Year: 2016).*

(Continued)

*Primary Examiner* — Amy C Bonaparte
(74) *Attorney, Agent, or Firm* — Klarquist Sparkman, LLP

(57) ABSTRACT

The method of the present invention for converting a nitrile functional group into a hydroxamic acid functional group can be easily performed at room temperature and under normal pressure by using a peroxocobalt complex. The final hydroxamic acid functional group produced through the intermediate Hydroximatocobalt (III) compound or the derivative comprising the same has been known to be able to inhibit the growth of cancer cells, so that the conversion method of the present invention can be applied to the preparation of a pro-drug for anticancer treatment.

10 Claims, 10 Drawing Sheets

(56) References Cited

OTHER PUBLICATIONS

Cho ("Synthesis, Structural, and Spectroscopic Characterization and Reactivities of Mononuclear CobatI(III)-Peroxo Complexes" J. Am. Chem. Soc., 2010, 132, p. 16977-16986) (Year: 2010).*
Noh ("Distinct Reactivity of a Mononuclear Peroxocobalt(III) Species toward Activation of Nitriles", J. Am. Chem. Soc., 2017, 139, p. 10960-10963) (Year: 2017).*
Kobayashi and Shimizu, "Nitrile hydrolases," *Curr. Opin. Chem. Biol.* 4:95-102 (2000).

* cited by examiner

METHOD OF CONVERTING A NITRILE FUNCTIONAL GROUP INTO A HYDROXAMIC FUNCTIONAL GROUP BY USING A PEROXOCOBALT COMPLEX AT ROOM TEMPERATURE AND NORMAL PRESSURE

CROSS REFERENCE TO RELATED APPLICATIONS

This application claims priority under 35 U.S.C. § 119 to Korean Patent Application No. 10-2017-0130178, filed on Oct. 11, 2017, which is incorporated by reference herein in its entirety.

BACKGROUND OF THE INVENTION

1. Field of the Invention

The present invention relates to a method of converting a nitrile functional group into a hydroxamic acid functional group by using a peroxocobalt complex at room temperature and under normal pressure.

2. Description of the Related Art

Nitride is a useful substance used in a variety of industries. It has chemical versatility, so that it can be used as a useful precursor in the field of synthetic chemistry. In the field of biotechnology, this material can be used for the plant hormone biosynthesis. Nitrile is also used as an ingredient of herbicides, indicating that it is also used in the field of agriculture.

However, when nitrile remains in an industrial waste or environment, the environment can be contaminated. Therefore, the process of converting nitrile to other compounds is environmental important (non-patent reference 1). Studies have been undergoing for the conversion of nitrile into another functional group by activating nitrile. The nitrile group can be converted into various functional groups such as acetic acid and an amide group, etc.

Up to now, the reaction to activate the nitrile group is mostly an organic synthesis reaction requiring strong acid and strong base or high temperature conditions. The method to activate nitrile being used so far is to induce an organic synthesis reaction which requires a strong acid and a strong base or a high temperature. Particularly, nitrile is not easy to be activated because it has a strong triple bond of carbon and nitrogen. To induce the reaction easily and conveniently in various industrial fields, it is important to develop a method to active nitrile under mild conditions like room temperature and normal pressure. So, studies have been undergoing to activate nitrile under mild conditions.

In particular, the enzymes involved in nitrite in vivo can react under relatively mild conditions. Therefore, a catalyst developed by mimicking the enzymes can be applied to various industrial fields. For this purpose, various mimetic compounds have been used to disclose the mechanism of the enzyme reaction.

The method for activating nitrile of the present invention is based on cobalt peroxo species. The cobalt peroxo compound previously discovered is known to be capable of a nucleophilic reaction such as aldehyde deformylation.

Hydroximatocobalt (III), the intermediate compound produced through the method for activating nitrile according to the present invention, can be studied as an inhibitor of a specific enzyme over-expressed in cancer cells. The intermediate herein turns into cobalt (II) that is easily chemically modified through reduction in vivo with releasing a hydroxymate functional group. The released hydroxymate group has chelating properties so that it can bind to zinc in the active site of the matrix metalloproteinase over-expressed in cancer cells, indicating that it can inhibit the growth of cancer cells.

Therefore, the intermediate and the final product of the activation reaction of nitrile can be used as a pro-drug that can deliver the hydroxymate functional group safely and selectively to cancer cells.

PRIOR ART REFERENCE

Non-Patent Reference (Non-patent Reference 1) Curr. Opin. Chem. Biol. 4, 95-102 (2000)

SUMMARY OF THE INVENTION

It is an object of the present invention to provide a method of converting a nitrile functional group into a hydroxamic acid functional group in the presence of a peroxocobalt complex.

It is another object of the present invention to provide the peroxocobalt complex above.

To achieve the above objects, the present invention provides a method of converting a nitrile functional group (—C≡N) into a hydroxamic acid functional group

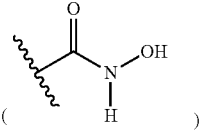

in the presence of a peroxocobalt complex represented by formula 1 below.

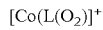 [Formula 1]

(In formula 1,
L is

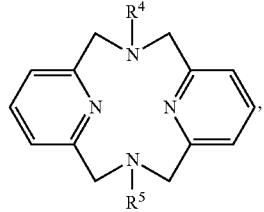

$R^4$ and $R^5$ are independently straight or branched $C_{1-10}$ alkyl, substituted or unsubstituted $C_{3-10}$ cycloalkyl, or substituted or unsubstituted $C_{6-10}$ aryl, wherein, the substituted $C_{3-10}$ cycloalkyl or the substituted $C_{6-10}$ aryl is the $C_{3-10}$ cycloalkyl or the $C_{6-10}$ aryl substituted with one or more substituents selected from the group consisting of halogen, —OH, —CN, —NO$_2$, straight or branched $C_{1-5}$ alkyl and straight or branched $C_{1-5}$ alkoxy).

The present invention also provides a method of converting a compound containing a nitrile functional group (—C≡N) represented by formula 2 below into a compound containing a hydroxamic acid functional group

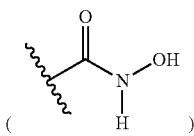

represented by formula 3 in the presence of a peroxocobalt complex represented by formula 1 below, as shown in reaction formula 1 below.

[Reaction Formula 1]

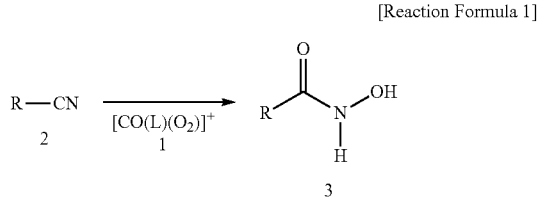

(In reaction formula 1,
L is

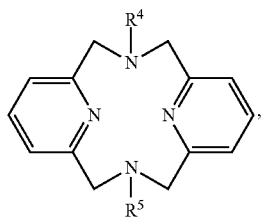

$R^4$ and $R^5$ are independently straight or branched $C_{1-10}$ alkyl, substituted or unsubstituted $C_{3-10}$ cycloalkyl, or substituted or unsubstituted $C_{6-10}$ aryl, wherein, the substituted $C_{3-10}$ cycloalkyl or the substituted $C_{6-10}$ aryl is the $C_{3-10}$ cycloalkyl or the $C_{6-10}$ aryl substituted with one or more substituents selected from the group consisting of halogen, —OH, —CN, —NO$_2$, straight or branched $C_{1-5}$ alkyl and straight or branched $C_{1-5}$ alkoxy, R is

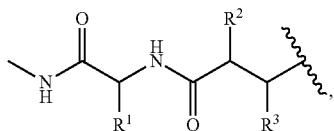

aliphatic hydrocarbon group, or aromatic hydrocarbon group, $R^1$, $R^2$ and $R^3$ are independently —OH, straight or branched $C_{1-10}$ alkyl, straight or branched $C_{1-10}$ alkoxy, substituted or unsubstituted $C_{3-10}$ cycloalkyl, or substituted or unsubstituted $C_{6-10}$ aryl, wherein, the substituted $C_{3-10}$ cycloalkyl or the substituted $C_{6-10}$ aryl is the $C_{3-10}$ cycloalkyl or the $C_{6-10}$ aryl substituted with one or more substituents selected from the group consisting of halogen, —OH, —CN, —NO$_2$, straight or branched $C_{1-5}$ alkyl and straight or branched $C_{1-5}$ alkoxy).

In addition, the present invention provides a peroxocobalt complex represented by formula 1 below.

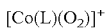 [Formula 1]

(In formula 1,
L is

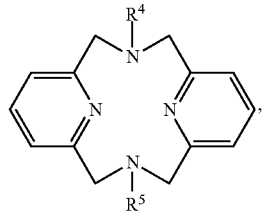

$R^4$ and $R^5$ are independently straight or branched $C_{1-10}$ alkyl, substituted or unsubstituted $C_{3-10}$ cycloalkyl, or substituted or unsubstituted $C_{6-10}$ aryl, wherein, the substituted $C_{3-10}$ cycloalkyl or the substituted $C_{6-10}$ aryl is the $C_{3-10}$ cycloalkyl or the $C_{6-10}$ aryl substituted with one or more substituents selected from the group consisting of halogen, —OH, —CN, —NO$_2$, straight or branched $C_{1-5}$ alkyl and straight or branched $C_{1-5}$ alkoxy).

Advantageous Effect

The method of the present invention for converting a nitrile functional group into a hydroxamic acid functional group can be easily performed at room temperature and under normal pressure by using a peroxocobalt complex. The final hydroxamic acid functional group produced through the intermediate Hydroximatocobalt (III) compound or the derivative comprising the same has been known to be able to inhibit the growth of cancer cells, so that the conversion method of the present invention can be applied to the preparation of a pro-drug for anticancer treatment.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
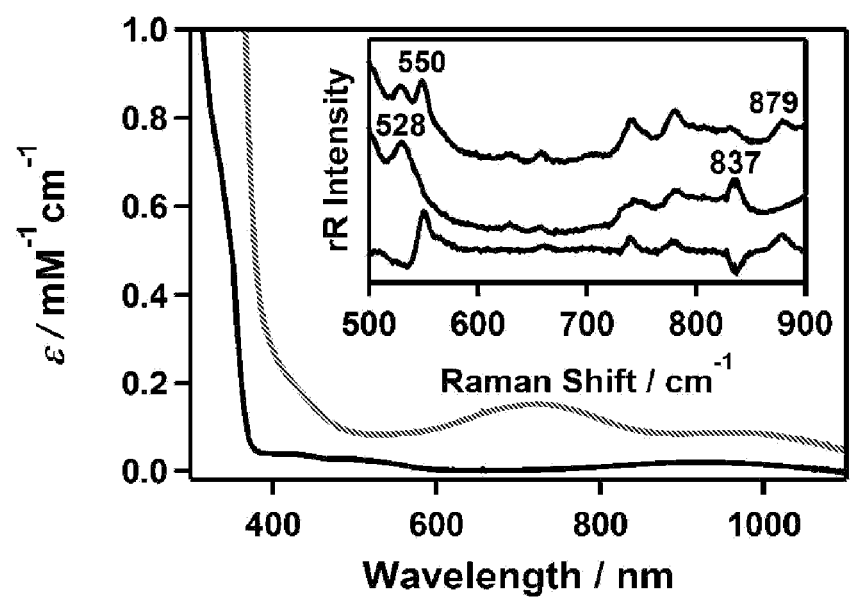
FIG. 1 is a graph illustrating the electron absorption spectrum of the complex of Example (gray line) and the composite of Preparative Example (dark black line) which is the precursor of the complex of Example 1. The insert on the top right presents the resonance Raman spectrum: 1-$^{16}$O (16 mM; top most line); 1-$^{18}$O (16 mM; middle line); The difference spectrum between 1-$^{16}$O and 1-$^{18}$O (bottom line) was obtained by excitation at 355 nm in CH$_3$CN at 30⌐. 1-$^{16}$O and 1-$^{18}$O were obtained by the same manner as described in Example 1 by using H$_2$$^{16}$O$_2$ and H$_2$$^{18}$O$_2$, respectively.

Hereinafter, the present invention is described in detail.

The present invention provides a method of converting a nitrile functional group (—C≡N) into a hydroxamic acid functional group

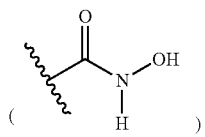

in the presence of a peroxocobalt complex represented by formula 1 below.

[Co(L)(O$_2$)]$^+$           [Formula 1]

In formula 1,
L is

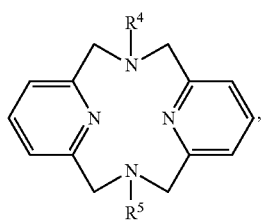

R$^4$ and R$^5$ are independently straight or branched C$_{1-10}$ alkyl, substituted or unsubstituted C$_{3-10}$ cycloalkyl, or substituted or unsubstituted C$_{6-10}$ aryl, wherein, the substituted C$_{3-10}$ cycloalkyl or the substituted C$_{6-10}$ aryl is the C$_{3-10}$ cycloalkyl or the C$_{6-10}$ aryl substituted with one or more substituents selected from the group consisting of halogen, —OH, —CN, —NO$_2$, straight or branched C$_{1-5}$ alkyl and straight or branched C$_{1-5}$ alkoxy.

At this time, the R$^4$ and R$^5$ are independently t-butyl or cyclohexyl.

The present invention also provides a method of converting a compound containing a nitrile functional group (—C≡N) represented by formula 2 below into a compound containing a hydroxamic acid functional group

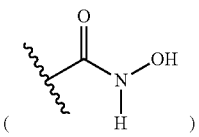

represented by formula 3 in the presence of a peroxocobalt complex represented by formula 1 below, as shown in reaction formula 1 below.

[Reaction Formula 1]

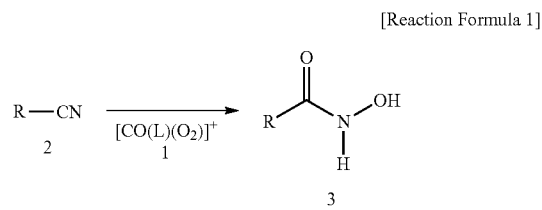

In reaction formula 1,
L is

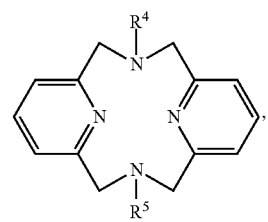

R$^4$ and R$^5$ are independently straight or branched C$_{1-10}$ alkyl, substituted or unsubstituted C$_{3-10}$ cycloalkyl, or substituted or unsubstituted C$_{6-10}$ aryl, wherein, the substituted C$_{3-10}$ cycloalkyl or the substituted C$_{6-10}$ aryl is the C$_{3-10}$ cycloalkyl or the C$_{6-10}$ aryl substituted with one or more substituents selected from the group consisting of halogen, —OH, —CN, —NO$_2$, straight or branched C$_{1-5}$ alkyl and straight or branched C$_{1-5}$ alkoxy, R is

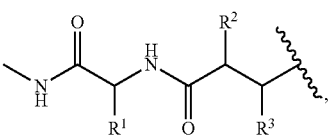

aliphatic hydrocarbon group, or aromatic hydrocarbon group, $R^1$, $R^2$ and $R^3$ are independently —OH, straight or branched $C_{1-10}$ alkyl, straight or branched $C_{1-10}$ alkoxy, substituted or unsubstituted $C_{3-10}$ cycloalkyl, or substituted or unsubstituted $C_{6-10}$ aryl, wherein, the substituted $C_{3-10}$ cycloalkyl or the substituted $C_{6-10}$ aryl is the $C_{3-10}$ cycloalkyl or the $C_{6-10}$ aryl substituted with one or more substituents selected from the group consisting of halogen, —OH, —CN, —NO$_2$, straight or branched $C_{1-5}$ alkyl and straight or branched $C_{1-5}$ alkoxy.

In an aspect of the present invention, the aliphatic hydrocarbon group is straight or branched $C_{1-10}$ alkyl or substituted or unsubstituted $C_{3-10}$ cycloalkyl, and at this time the substituted $C_{3-10}$ cycloalkyl is the $C_{3-10}$ cycloalkyl substituted with one or more substituents selected from the group consisting of halogen, —OH, —CN, —NO$_2$, straight or branched $C_{1-5}$ alkyl and straight or branched $C_{1-5}$ alkoxy; and the aromatic hydrocarbon group is substituted or unsubstituted $C_{6-10}$ aryl, and at this time the substituted $C_{6-10}$ aryl is the $C_{6-10}$ aryl substituted with one or more substituents selected from the group consisting of halogen, —OH, —CN, —NO$_2$, straight or branched $C_{1-5}$ alkyl and straight or branched $C_{1-5}$ alkoxy.

In another aspect of the present invention, the aliphatic hydrocarbon group is straight or branched $C_{1-5}$ alkyl or substituted or unsubstituted $C_{3-8}$ cycloalkyl, and at this time the substituted $C_{3-8}$ cycloalkyl is the $C_{3-8}$ cycloalkyl substituted with one or more substituents selected from the group consisting of straight or branched $C_{1-3}$ alkyl and straight or branched $C_{1-3}$ alkoxy; and the aromatic hydrocarbon group is substituted or unsubstituted $C_6$ aryl, and at this time the substituted $C_6$ aryl is the $C_6$ aryl substituted with one or more substituents selected from the group consisting of straight or branched $C_{1-3}$ alkyl and straight or branched $C_{1-3}$ alkoxy.

In another aspect of the present invention, the aliphatic hydrocarbon group is —CH$_3$ or —CH$_2$CH$_3$; and the aromatic hydrocarbon group is -Ph.

In another aspect of the present invention, the $R^1$, $R^2$ and $R^3$ are independently —OH or straight or branched $C_{1-5}$ alkyl; the $R^1$ and $R^2$ are t-butyl; and the $R^3$ is —OH.

When a compound containing a nitrile functional group (—C≡N) is converted into a compound containing a hydroxamic acid functional group in the presence of a peroxocobalt complex, the complex represented by formula 4 below is produced as an intermediate.

[Formula 4]

$$[CO(L)(R—C(=NO)O)]^+ \quad \quad 4$$

In formula 4,
L and R are as defined above.

Hydroximato ligands, the tautomers of hydroxamato analogue, have been used for the treatment of cancer and Alzheimer's disease because they can act as inhibitors of metalloenzymes.

[Relational Expression of Hydroxamato and Hydroximato Tautomer]

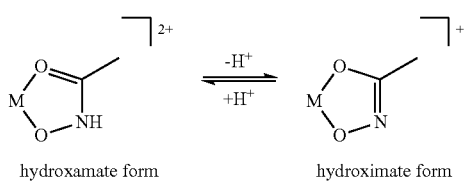

hydroxamate form    hydroximate form

The hydroximato cobalt complex represented by formula (4) is also referred to as a hydroximatocobalt (III) compound, which can be converted into cobalt (II) in vivo through reduction that can be easily chemically modified, resulting in the release of a hydroxymate functional group, more precisely a hydroxamic acid functional group

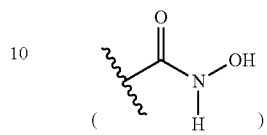

or a derivative comprising the same.

The released hydroxymate functional group has chelating properties so that it can bind to zinc in the active site of the matrix metalloproteinase over-expressed in cancer cells, indicating that it can inhibit the growth of cancer cells. Therefore, the final product of the activation reaction of nitrile can be used as a pro-drug that is a carrier which can deliver the hydroxymate functional group safely and selectively to cancer cells by taking advantage of the difference of cell potential between normal cells and cancer cells. Marimastat having the structure below is an example of well informed anticancer drugs containing the hydroxamic acid functional group.

[Chemical structure of Marimastat]

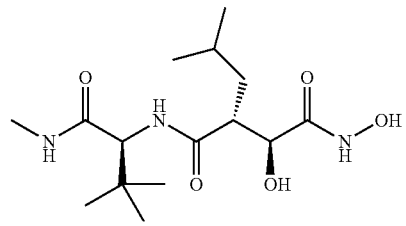 [SMILES: CNC(=O)[C@@H](NC(=O)[C@H](CC(C)C)[C@H](O)C(=O)NO)C(C)(C)C]

In a preferred embodiment of the present invention, the present invention provides a method of converting a compound containing a nitrile functional group (—C≡N) represented by formula 2 into a hydroximato cobalt complex represented by formula 4 in the presence of a peroxocobalt complex represented by formula 1, as shown in reaction formula 2.

[Reaction Formula 2]

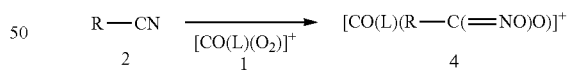

In reaction formula 2,
R and L are as defined above.

The conversion method above can be performed at room temperature under normal pressure to ensure a high yield. At this time, the room temperature can be 0□~50□, 0□~40□, 0□~30□, 0□~25□, 10□~50□, 20□~50□, and 25□~50□. The normal pressure herein can be 0.1~3 atm, 0.1~2 atm, 0.1~1.5 atm, 0.1~1 atm, 0.5~3 atm, 0.7~3 atm, 0.9~3 atm, and 1~3 atm.

In addition, the present invention provides a peroxocobalt complex represented by formula 1 below.

$$[Co(L(O_2)]^+ \quad \quad \text{[Formula 1]}$$

In formula 1,
L is as defined above.

The peroxocobalt complex represented by formula 1 above can be effectively used for the activation of nitrile according to the present invention.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: Preparation of [Co$^{II}$(TBDAP)(NO$_3$)(H$_2$O)](NO$_3$)

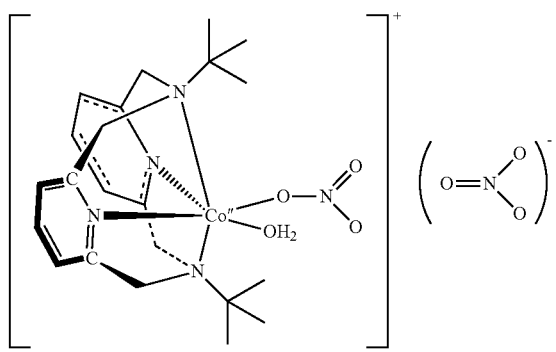

Co(NO$_3$)$_2$.6H$_2$O (0.146 g, 0.50 mmol) and TBDAP(N,N'-di-tertbutyl-2,11-diaza[3.3] (2,6)-pyridinophane, 0.176 g, 0.50 mmol) were added to CH$_3$CN (2.0 mL) and CHCl$_3$ (2.0 mL), followed by stirring for 12 hours and as a result a pink solution was obtained. Et$_2$O (40 mL) was added thereto, followed by filtering, washing and drying in vacuo. As a result, the target compound was obtained as a pink powder. Yield: 94% (0.2610 g). Crystallographically appropriate X ray crystals were obtained by diffusing Et$_2$O slowly in CH$_3$CN containing the target compound dissolved therein.

ESI-MS in CH$_3$CN: m/z 205.6 for [Co(TBDAP)]$^{2+}$, m/z 226.1 for [Co(TBDAP)(CH$_3$CN)]$^{2+}$, and m/z 246.7 for [Co(TBDAP)(CH$_3$CN)$_2$]$^{2+}$, m/z 473.2 for [Co(TBDAP)(NO$_3$)]+. Anal. Calcd for C$_{22}$H$_{34}$CoN$_6$O$_7$: C, 47.74; H, 6.19; N, 15.18. Found: C, 47.62; H, 6.194; N, 15.29. Effective magnetic moment μeff=3.9 B.M. (measured by 1H NMR Evans method in CH$_3$CN at 25□)

Example 1: Preparation of Peroxocobalt Complex [Co(TBDAP)(O$_2$)] (1)

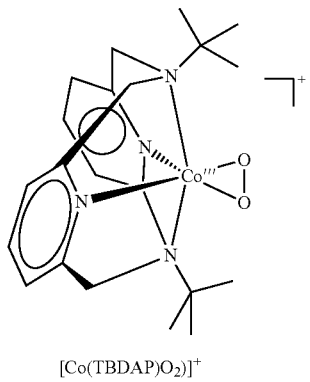

[Co(TBDAP)(NO$_3$)(H$_2$O)](NO$_3$) (0.0277 g, 0.050 mmol) prepared in Preparative Example 1 was treated with H$_2$O$_2$ (5.0 eq) in the presence of triethylamine (TEA; 2 eq) dissolved in CH$_3$CN (1.5 mL) at ~40□, resulting in the preparation of a green solution. Et$_2$O (40 mL) was added thereto, followed by filtering, washing and drying in vacuo. As a result, a green powder was obtained. The obtained green powder was dissolved in CHCl$_3$ at −40□. Et$_2$O was slowly dispersed in the solution obtained at −40□ above, and as a result [Co(TBDAP)(O$_2$)](NO$_3$)(H$_2$O)$_2$ (1-NO$_3$.2H$_2$O) was obtained as a green crystal. Crystal yield: 72% (0.0157 g).

Crystallographically appropriate X ray crystals of [Co(TBDAP)(O$_2$)](BPh$_4$)(1-BPh$_4$) formed by anion exchange with BPh$_4$- in 1-NO$_3$.2H$_2$O complex were obtained by dispersing Et$_2$O slowly in CHCl$_3$ solution of 1 in the presence of NaBPh$_4$ (0.17 g).

On the other hand, [Co(TBDAP)($^{18}$O$_2$)]$^+$ (1-$^{18}$O$_2$) can be prepared by treating [Co(TBDAP)(NO$_3$)(H$_2$O)](NO$_3$) (2.0 mM) prepared in Preparative Example 1 with H$_2^{18}$O$_2$ (5.0 eq, 36 μL, 95% $^{18}$O-enriched, 2.2% H$_2^{18}$O$_2$, dissolved in water) in the presence of triethylamine(TEA; 2 eq) dissolved in CH$_3$CN (2.0 mL) at −40□.

Figure 2:
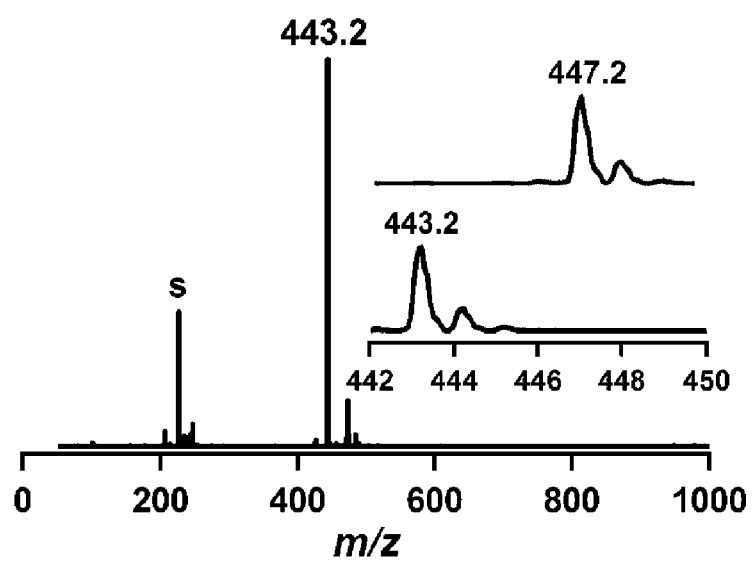
FIG. 2 is a graph illustrating the ESI-MS spectrum of the complex of Example 1 (1) in CH$_3$CN at −20□. The peak at m/z=443.2 corresponds to [Co$^{III}$(TBDAP)(O$_2$)]$^+$ (1-$^{16}$O; calcd. m/z=443.2). The insert on the top right indicates the isotope distribution pattern observed at the peaks of the followings: 1-$^{16}$O (lower) is m/z=443.2/1-$^{18}$O (upper) is m/z=447.2.

ESI-MS CH$_3$CN (see FIGS. 1 and 2): m/z 443.2 for [Co(TBDAP)(O$_2$)]$^+$. Anal. Calcd for C$_{46}$H$_{52}$BCoN$_4$O: C, 48.80; H, 6.70; N, 12.93. Found: C, 48.67; H, 6.31; N, 12.91.

Experimental Example 1: Preparation of Hydroximato Cobalt Complex [Co(TBDAP)(CH$_3$C(—NO)O] (2)

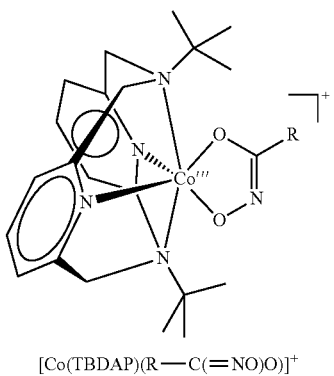

R = Me

1-NO$_3$.2H$_2$O (0.0234 g, 0.046 mmol) prepared in Example 1 was dissolved in 1.5 mL of CH$_3$CN. The mixed solution was kept at 25□ overnight to induce the color change from green to dark brown. Et$_2$O was slowly dispersed in the mixed solution and as a result [Co(TBDAP)(CH$_3$C(=NO)O]—NO$_3$.H$_2$O (2-NO$_3$.H$_2$O) complex was obtained as a brown crystal. At this time, the crystal yield was 54% (0.0139 g).

Crystallographically appropriate X ray crystals of 2-BPh$_4$ formed by anion exchange with BPh$_4$- in 2-NO$_3$.H$_2$O complex were obtained by dispersing Et$_2$O slowly in CH$_3$CN solution containing 2 dissolved therein in the presence of NaBPh$_4$ (0.17 g).

On the other hand, [Co(TBDAP)(CH₃C(=N¹⁸O)¹⁸O]⁺ can be prepared by reacting 1-¹⁸O₂ with CH₃CN (2.0 mL) at 25□.

ESI-MS CH₃CN (see FIGS. 3 and 4): m/z 484.3 for [Co(TBDAP)(CH₃C(=NO)O)]⁺. FT-IR (ATR): 1523 cm⁻¹ (w, C=N). Anal. Calcd for C₂₄H₃₇BCoN₆O₆: C, 51.06; H, 6.61; N, 14.89. Found: C, 51.19; H, 6.58; N, 14.79.

Figure 3:
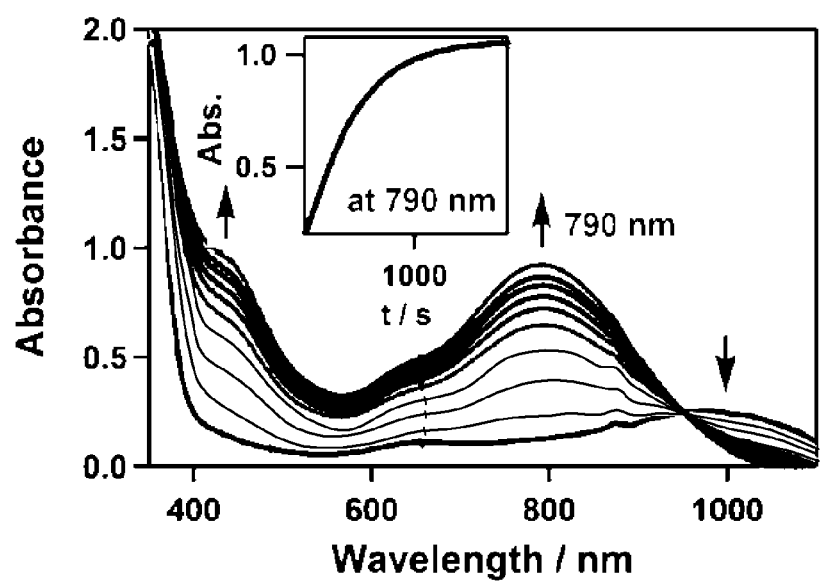
FIG. 3 is a graph illustrating the changes of the UV-vis spectra observed according to the reaction of the complex of Example 1 (2.0 mM) with CH$_3$CN (3.8 M) in C$_6$H$_6$ at 40□ in Experimental Example 1. The insert on the top right presents the absorption changes of 790 nm wavelength band due to the generation of [Co(TBDAP)(CH$_3$C(=NO)O] (2).

As shown in FIG. 3, the absorption band at 974 nm produced by Example 1 (1) disappeared with first-order kinetics. The generated (2) corresponds to electronic absorption bands at λ$_{max}$=450 (ε=420 M⁻¹ cm¹) and 790 nm (ε=430 M¹ cm¹), and appeared as an isosbestic point at 960 nm.

Figure 4:
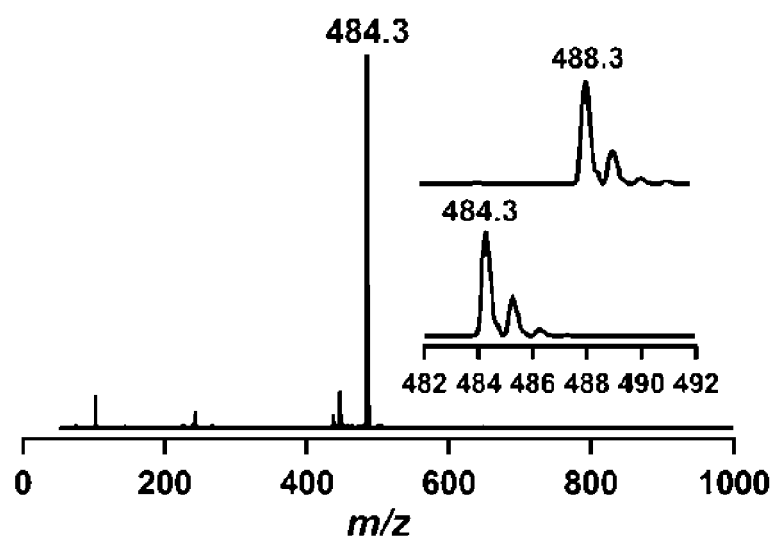
FIG. 4 shows the ESI-MS spectrum of the solution wherein the complex of Example 1 (2.0 mM) reacted to CH$_3$CN (3.8 M) in C$_6$H$_6$ at 40⌐ in Experimental Example 1. The peak at m/z=484.3 corresponds to [Co$^{III}$(TBDAP) (CH$_3$C(=NO)O)]$^+$ (2-$^{16}$O) (calculated m/z of 484.2). The insert on the top right indicates the isotope distribution pattern measured with 2-$^{16}$O (lower) and 2-$^{18}$O (upper) induced from 1-$^{16}$O and 1-$^{18}$O, respectively.

As shown in FIG. 4, the ESl-MS spectrum of (2) obtained above showed an important signal at m/z=484.3, which was confirmed to correspond to [Co(TBDAP)(CH3C(=NO)O)]⁺ (2-¹⁶O; calculated m/z of 484.2). ¹⁸O-labeling was also performed. The results are shown in the insert of FIG. 4, from which, it was confirmed that the oxygen atom of (2) was induced from the peroxo group of Example 1.

Experimental Example 2: Preparation of Hydroximato Cobalt Complex [Co(TBDAP)(CH₃CH₂C(=NO)O] (3)

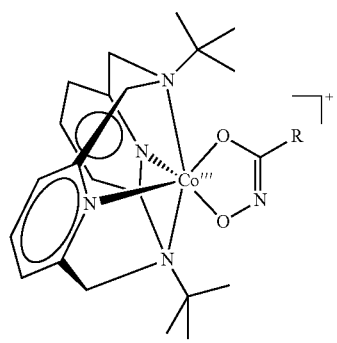

[Co(TBDAP)(R—C(=NO)O)]⁺
R = Et (3)

1-BPh₄ (0.0172 g, 0.034 mmol) prepared in Example 1 was dissolved in 1.5 mL of CH₃CH₂CN. The mixed solution was kept at 25□ overnight to induce the color change from green to dark brown. Et₂O was slowly dispersed in the mixed solution in the presence of NaBPh₄ (0.17 g) and as a result [Co(TBDAP)(CH₃CH₂C(=NO)O]—BPh₄ (3-BPh₄) complex was obtained as a brown crystal. At this time, the crystal yield was 46% (0.0088 g).

On the other hand, [Co$^{III}$(TBDAP)(CH₃CH₂C(=N¹⁸O) ¹⁸O]⁺ can be prepared by reacting 1-¹⁸O₂ with CH₃CH₂CN (2.0 mL) at 25□.

Figure 5:
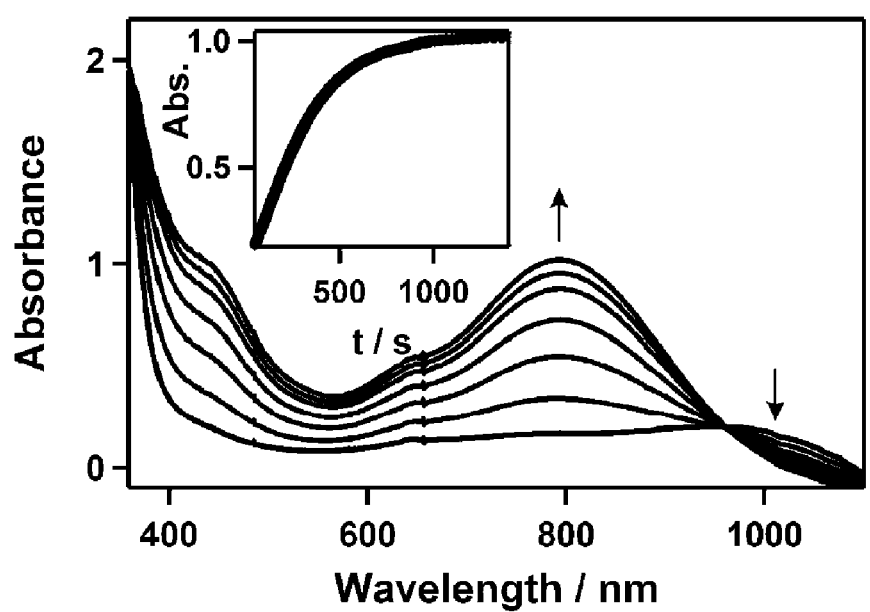
FIG. 5 is a graph illustrating the changes of the UV-vis spectra observed according to the reaction of the complex of Example 1 (2.0 mM) with CH$_3$CH$_2$CN (1.4 M) in CHCl$_3$ at 40□ in Experimental Example 2. The insert on the top right presents the absorption changes of 790 nm wavelength band due to the generation of [Co(TBDAP)(CH$_3$CH$_2$C(=NO)O] (3).
Figure 6:
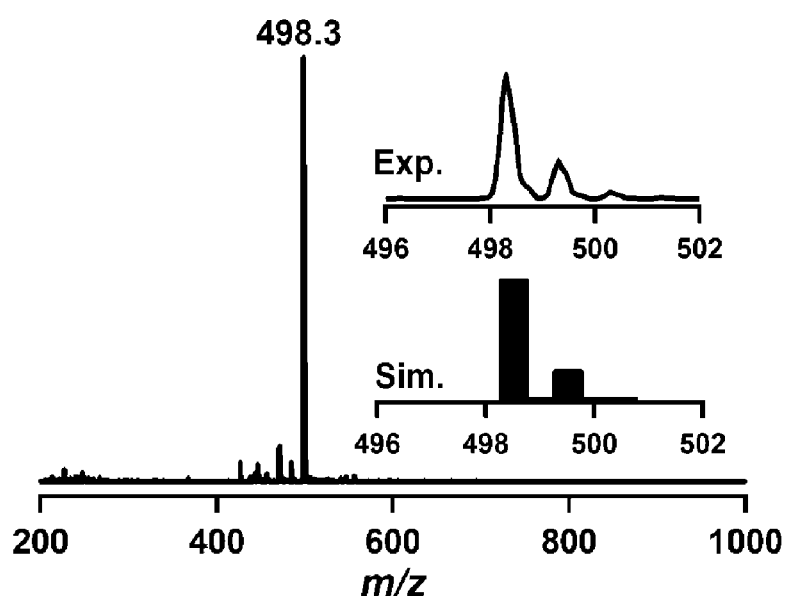
FIG. 6 shows the ESl-MS spectrum of the solution wherein the complex of Example 1 (2.0 mM) reacted to CH$_3$CH$_2$CN (1.4 M) in CHCl$_3$ at 40□ in Experimental Example 2. The peak at m/z=498.3 corresponds to [Co$^{III}$(TBDAP)(CH$_3$CH$_2$C(=NO)O)]$^+$ (calculated m/z of 498.2). The insert on the top right indicates the isotope distribution pattern measured (upper) at the peak of m/z=498.3 and calculated.

ESI-MS CH₃CN (see FIGS. 5 and 6): m/z 498.3 for [Co(TBDAP)(CH₃CH₂C(=NO)O]⁺. FT-IR (ATR): 1523 cm⁻¹ (w, C=N). Anal. Calcd. for C₄₉H₅₇BCoN₅O₂: C, 71.97; H, 7.03; N, 8.56. Found: C, 71.95; H, 7.23; N, 8.4.

Experimental Example 3: Preparation of Hydroximato Cobalt Complex [Co(TBDAP)(C₆H₅C(=NO)O] (4)

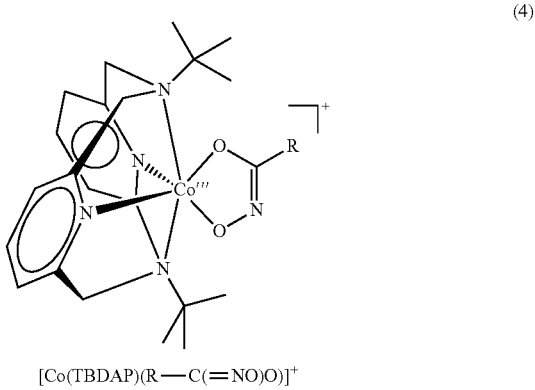

[Co(TBDAP)(R—C(=NO)O)]⁺
R = Ph (4)

1-BPh₄ (0.0186 g, 0.037 mmol) prepared in Example 1 was dissolved in 1.5 mL of C₆H₅CN. The mixed solution was kept at 25□ overnight to induce the color change from green to dark brown. The yield of the obtained [Co(TBDAP)(C₆H₅C(=NO)O]—BPh₄.H₂O powder was 40% (0.0128 g). Et₂O was slowly dispersed in the mixed solution whose color was changed into dark brown in the presence of NaBPh₄ (0.17 g), during which water molecules were eliminated and as a result [Co(TBDAP)(C₆H₅(=NO)O]—BPh₄ (4-BPh₄), the crystallographically appropriate X-ray crystal, was obtained.

On the other hand, [Co$^{III}$(TBDAP)(C₆H₅ (—N¹⁸O)¹⁸O]⁺ can be prepared by reacting 1-¹⁸O₂ with C₆H₅CN (2.0 mL) at 25□.

Figure 7:
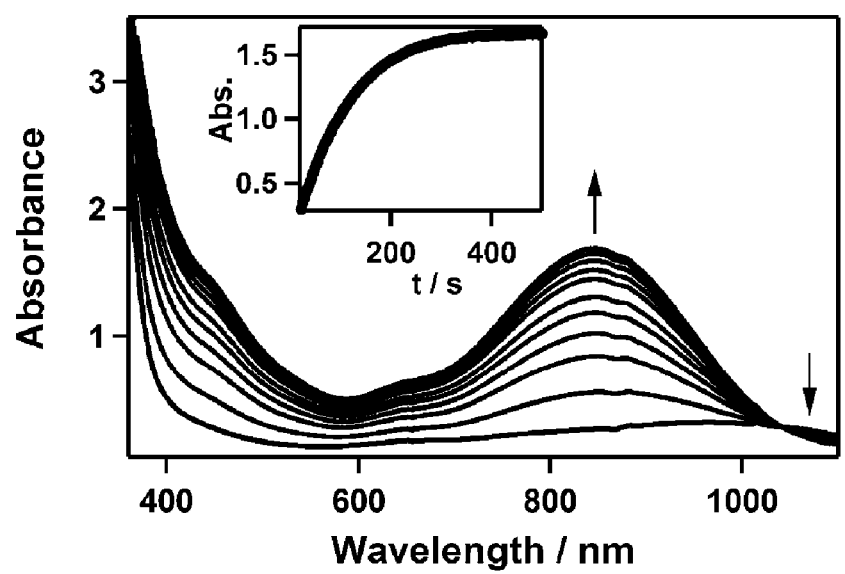
FIG. 7 is a graph illustrating the changes of the UV-vis spectra observed according to the reaction of the complex of Example 1 (2.0 mM) with C$_6$H$_5$CN (0.98 M) in CHCl$_3$ at 40□ in Experimental Example 3. The insert on the top right presents the absorption chances of 840 nm wavelength band due to the generation of [Co(TBDAP)(C$_6$H$_5$C(=NO)O] (4).
Figure 8:
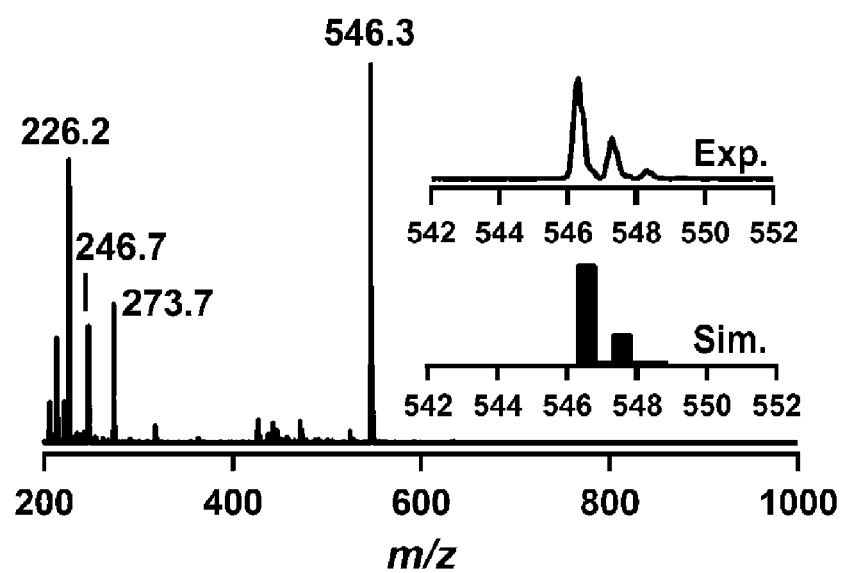
FIG. 8 shows the ESl-MS spectrum of the solution wherein the complex of Example 1 (2.0 mM) reacted to C$_6$H$_5$CN (0.98 M) in CHCl$_3$ at 40□ in Experimental Example 3. The peak at m/z=546.3 corresponds to [Co$^{III}$(TBDAP)(C$_6$H$_5$C(=NO)O)]$^+$ (calculated m/z of 546.2). The insert on the top right indicates the isotope distribution pattern measured (upper) at the peak of m/z=546.3 and calculated.

ESI-MS CH3CN (see FIGS. 7 and 8): m/z 546.3 for [Co(TBDAP)(C₆H₅C(=NO)O)]⁺. FT-IR (ATR): 1546 cm⁻¹ (w, C=N). Anal. Calcd. for C₅₃H₅₉BCoN₅O₃: C, 72.03; H, 6.73; N, 7.92. Found: C, 71.96; H, 6.86; N, 7.91.

Experimental Example 4: Evaluation of Reactivity to Para-Substituted Benzonitrile To evaluate the reactivity of the peroxocobalt complex [Co(TBDAP)(O₂)] (1) prepared in Example 1 to para-substituted benzonitrile, reaction was induced at 40□ by the same manner as described in Experimental Example 2 except that para-substituted benzonitrile was used instead of CH₃CH₂CN. At this time, —OMe, Me, H, and Cl were used as para-substituted substituents.

Upon completion of the reaction, k$_{obs}$ was measured by pseudo-first order fitting of kinetic data. The results are shown in FIG. 9.

Figure 9:
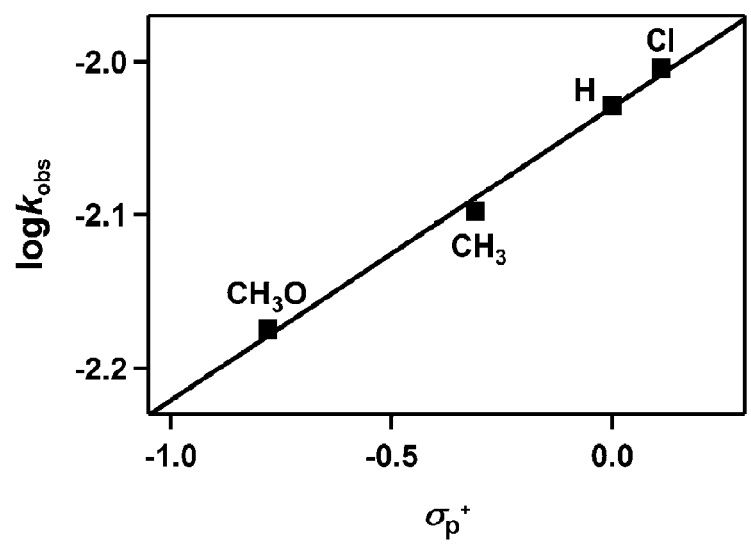
FIG. 9 presents the Hammett plot of log k$_{obs}$ for σ$_p^+$, the Hammett parameter.

FIG. 9 presents the Hammett plot of log k$_{obs}$ for σ$_p^+$, the Hammett parameter.

As shown in FIG. 9, the ρ value was measured as 0.18, and this small ρ value indicated that the reaction did not depend on the flow of electrons into the ring.

Particularly, the Hammett constant presenting the electrostatic property was 0.18, which was close to 0. The Hammet constant is positive when the reaction is nucleophilic, while it is negative when the reaction is electrophilic.

Figure 10:
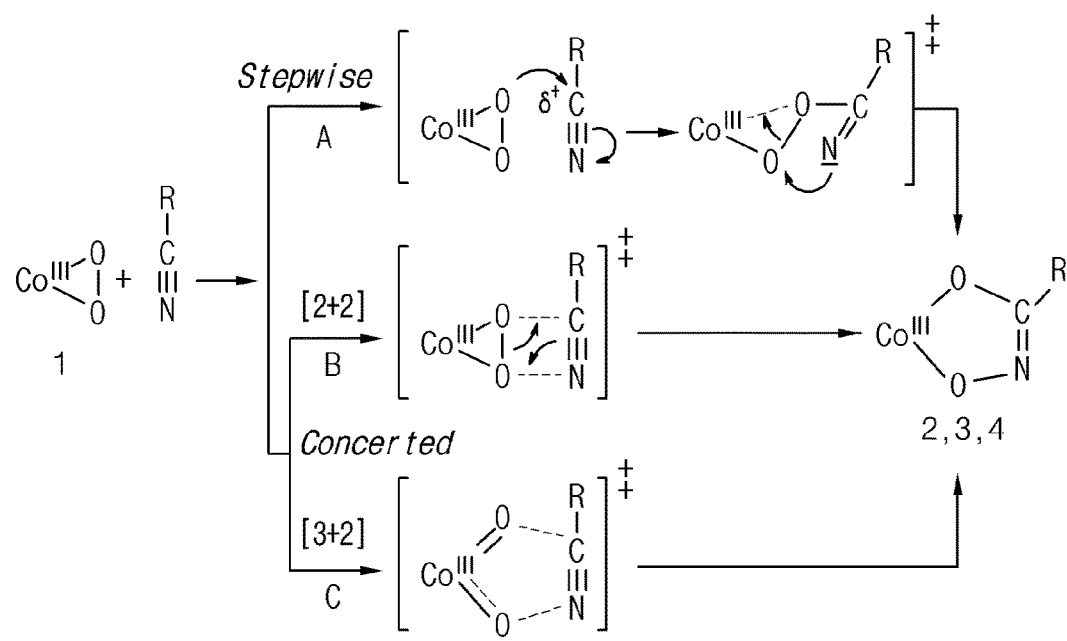
FIG. 10 presents the mechanism of nitrile activation according to the present invention.

However, the nitrile reaction which shows the Hammet constant of almost 0 undergoes a different transition state from the common nucleophilic reaction of metal-peroxo species. FIG. 10 presents the mechanism of nitrile activation according to the present invention.

The result that the Hammett constant above was close to o and the result of isotope labeling proving that the exchange reaction with external oxygen did not occur suggested that the mechanism was not a progressive transition state stepwise but a simultaneous reaction state.

What is claimed is:

1. A method of converting a nitrile functional group (—C≡N) into a hydroxamic acid functional group

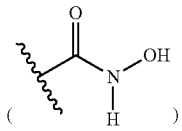

in the presence of a peroxocobalt complex represented by formula 1 below:

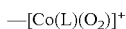 [Formula 1]

wherein,
L is

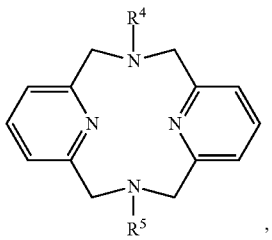

and $R^4$ and $R^5$ are independently straight or branched $C_{1-10}$ alkyl, substituted or unsubstituted $C_{3-10}$ cycloalkyl, or substituted or unsubstituted $C_{6-10}$ aryl, and wherein, the substituted $C_{3-10}$ cycloalkyl or the substituted $C_{6-10}$ aryl is a $C_{3-10}$ cycloalkyl or $C_{6-10}$ aryl, respectively, substituted with one or more substituents selected from the group consisting of halogen, —OH, —CN, —NO$_2$, straight or branched $C_{1-5}$ alkyl and straight or branched $C_{1-5}$ alkoxy.

2. The method according to claim 1, wherein the $R^4$ and $R^5$ above are independently t-butyl or cyclohexyl.

3. A method of converting a compound comprising a nitrile functional group (—C≡N) represented by formula 2 below into a compound comprising a hydroxamic acid functional group

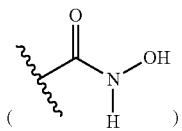 [SMILES: *C(=O)NO]

represented by formula 3 in the presence of a peroxocobalt complex represented by formula 1 below, as shown in reaction formula 1 below:

[Reaction Formula 1]

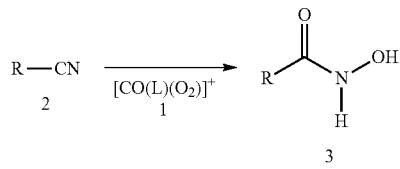

wherein
L is

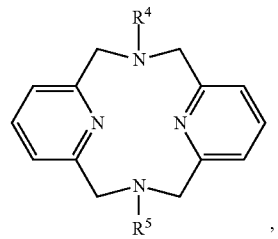

$R^4$ and $R^5$ are independently straight or branched $C_{1-10}$ alkyl, substituted or unsubstituted $C_{3-10}$, cycloalkyl, or substituted or unsubstituted $C_{6-10}$ aryl, wherein, the substituted $C_{3-10}$ cycloalkyl or the substituted $C_{6-10}$ aryl is $C_{3-10}$ cycloalkyl or $C_{6-10}$ aryl respectively, substituted with one or more substituents selected from the group consisting of halogen, —OH, —CN, —NO$_2$, straight or branched $C_{1-5}$ alkyl and straight or branched $C_{1-5}$ alkoxy, R is

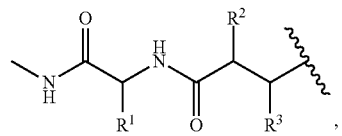

an aliphatic hydrocarbon group, or aromatic hydrocarbon group, $R^1$, $R^2$ and $R^3$ are independently OH, straight or branched $C_{1-10}$ alkyl, straight or branched $C_{1-10}$ alkoxy, substituted or unsubstituted $C_{3-10}$ cycloalkyl, or substituted or unsubstituted $C_{6-10}$ aryl, wherein, the substituted $C_{3-10}$ cycloalkyl or the substituted $C_{6-10}$ aryl is a $C_{3-10}$ cycloalkyl or a $C_{6-10}$ aryl, respectively, substituted with one or more substituents selected from the group consisting of halogen, —OH, —CN, —NO$_2$, straight or branched $C_{1-5}$ alkyl, straight $C_{1-5}$ alkoxy and branched $C_{1-5}$ alkoxy.

4. The method according to claim 3, wherein the aliphatic hydrocarbon group is straight $C_{1-10}$ alkyl, branched $C_{1-10}$ alkyl, substituted $C_{3-10}$ cycloalkyl, or unsubstituted $C_{3-10}$ cycloalkyl, and wherein the substituted $C_{3-10}$ cycloalkyl is a $C_{3-10}$ cycloalkyl substituted with one or more substituents, wherein the one or more substituents are halogen, —OH, —CN, —NO$_2$, straight $C_{1-5}$ alkyl, branched $C_{1-5}$ alkyl, straight $C_{1-5}$ alkoxy, or branched $C_{1-5}$ alkoxy; or wherein the aromatic hydrocarbon group is substituted or unsubstituted $C_{6-10}$ aryl, and wherein the substituted a $C_{6-10}$ aryl is $C_{6-10}$ aryl substituted with one or more substituents, wherein the one or more substituents are halogen, —OH, —CN, —NO$_2$, straight $C_{1-5}$ alkyl, branched $C_{1-5}$ alkyl, straight $C_{1-5}$ alkoxy, or branched $C_{1-5}$ alkoxy.

5. The method according to claim 3, wherein the aliphatic hydrocarbon group is straight $C_{1-5}$ alkyl, branched $C_{1-5}$ alkyl, substituted $C_{3-8}$ cycloalkyl, or unsubstituted $C_{3-8}$ cycloalkyl, and wherein the substituted $C_{3-8}$ cycloalkyl is a $C_{3-8}$ cycloalkyl substituted with one or more substituents, wherein the one or more substituents are straight $C_{1-3}$ alkyl, branched $C_{1-3}$ alkyl, straight $C_{1-3}$ alkoxy, or branched $C_{1-3}$ alkoxy; or wherein the aromatic hydrocarbon group is substituted or unsubstituted $C_6$ aryl, and wherein the substituted $C_6$ aryl is a $C_6$ aryl substituted with one or more substituents, wherein the one or more substituents are straight $C_{1-3}$ alkyl, branched $C_{1-3}$ alkyl, straight $C_{1-3}$ alkoxy or branched $C_{1-3}$ alkoxy.

6. The method according to claim 3, wherein the aliphatic hydrocarbon group is —$CH_3$ or —$CH_2CH_3$; or the aromatic hydrocarbon group is -Ph.

7. The method according to claim 3, wherein the $R^1$, $R^2$ and $R^3$ are independently —OH, straight $C_{1-5}$ alkyl, or branched $C_{1-5}$ alkyl.

8. The method according to claim 3, wherein the $R^1$ and $R^2$ are t-butyl; and the $R^3$ is —OH.

9. The method according to claim 3, wherein when the compound comprising the nitrile functional group (—C≡N) of formula 2 is converted into the compound comprising a hydroxamic acid functional group of formula 3 in the presence of the peroxocobalt complex of formula 1, a hydroximato cobalt complex represented by formula 4 below is produced as an intermediate:

[Formula 4]

$$[CO(L)(R\!-\!\!-\!C(\!=\!NO)O)]^+. \qquad 4$$

10. A peroxocobalt complex of the formula below:

$[Co(L)(O_2)]^+$ wherein

L is

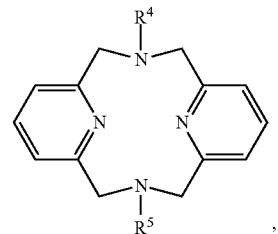

$R^4$ and $R^5$ are independently straight $C_{1-10}$ alkyl, branched $C_{1-10}$ alkyl, substituted $C_{3-10}$ cycloalkyl, unsubstituted $C_{3-10}$ cycloalkyl, substituted $C_{6-10}$ aryl or unsubstituted $C_{6-10}$ aryl, wherein the substituted $C_{3-10}$ cycloalkyl or the substituted $C_{6-10}$ aryl is a $C_{3-10}$ cycloalkyl or a $C_{6-10}$ aryl, respectively, substituted with one or more substituents, wherein the one or more substituents are halogen, —OH, —CN, —$NO_2$, straight $C_{1-5}$ alkyl, branched $C_{1-5}$ alkyl, straight $C_{1-5}$ alkoxy, or branched $C_{1-5}$ alkoxy.

* * * * *